United States Patent [19]

Feiring

[11] Patent Number: 5,536,754

[45] Date of Patent: Jul. 16, 1996

[54] FLUORINATED ION-EXCHANGE POLYMERS AND INTERMEDIATES THEREFOR

[75] Inventor: Andrew E. Feiring, Wilmington, Del.

[73] Assignee: E. I. Du Pont De Nemours and Company, Wilmington, Del.

[21] Appl. No.: 534,525

[22] Filed: Sep. 27, 1995

Related U.S. Application Data

[63] Continuation-in-part of Ser. No. 388,789, Feb. 15, 1995, Pat. No. 5,475,143.

[51] Int. Cl.$^6$ ............................. B01J 39/20; C08F 14/26; C08F 16/24

[52] U.S. Cl. ................. 521/32; 521/25; 521/30; 521/31; 521/33; 521/38; 526/243; 526/247; 568/39; 568/56; 502/168

[58] Field of Search ...................... 521/32, 38, 30, 521/31; 526/243, 247

[56] References Cited

U.S. PATENT DOCUMENTS

| | | | |
|---|---|---|---|
| 4,329,434 | 5/1982 | Kimoto | 521/27 |
| 4,555,369 | 11/1985 | Kimoto | 558/436 |
| 4,597,913 | 7/1986 | Kimoto | 558/436 |

*Primary Examiner*—Fred Zitomer

[57] ABSTRACT

Disclosed herein are partially fluorinated (co)polymers containing sulfonic acid or sulfonate salt groups, processes for making those polymers, and intermediates for those (co)polymers. The (co)polymers are useful as ion-exchange resins and (in the sulfonic acid form) acid catalysts.

12 Claims, No Drawings

FLUORINATED ION-EXCHANGE POLYMERS AND INTERMEDIATES THEREFOR

This is a continuation-in-part of Ser. No. 08/388,789, filed Feb. 15, 1995 now U.S. Pat. No. 5,475,143.

FIELD OF THE INVENTION

This invention concerns partially fluorinated sulfonic acid containing polymers suitable as ion-exchange resins and strong acid catalysts, and novel intermediates thereto.

TECHNICAL BACKGROUND

Polymers containing strongly acidic or basic groups are useful as ion-exchange resins, and for other uses. Sulfonic acid containing polymers are useful as ion-exchange resins and as strong acid catalysts. Polymers which are fluorinated may also be more thermally and/or chemically resistant than unfluorinated polymers, so fluorinated sulfonic acid containing polymers may be particularly useful. Such polymers are useful in the form of films, coatings, membranes, other shaped articles and particles.

For use as an ion exchange resin or strong acid catalyst resin, it is generally preferred if the resin contains as many active sites as possible. It is known in the art (see, for instance, U.S. Pat. No. 4,948,844) that it is difficult to (co)polymerize perfluorinated (alkyl vinyl ethers), while fluorinated alkyl vinyl ethers which contain some hydrogen in the alkyl group, particularly alpha to the ether oxygen, are more readily polymerizable, and can be (co)polymerized to give polymers with high vinyl ether contents.

Yu. E. Kirsh, et al., Russian Chemical Rev., vol. 59, p. 560–574 (1990) have reviewed the literature of perfluorinated cation exchange membranes.

U.S. Pat. No. 4,597,913 describes the synthesis of certain perfluorinated (with the exception of the "R" group on the sulfur) sulfide containing vinyl ethers, (co)polymers containing those vinyl ethers as repeat units, and oxidation of the (co)polymers to obtain the analogous sulfonic acid containing perfluorinated polymers. No mention is made of partially fluorinated sulfonic acid containing polymers.

T. Nguyen, et al., Eur. Polym. J., vol. 27, p. 435–438 (1991) describe the preparation of certain perfluorinated (with the exception of the "R" group on sulfur) sulfide containing vinyl ethers and their conversion to sulfonyl chlorides. No mention is made of the novel compounds described herein.

SUMMARY OF THE INVENTION

This invention concerns a copolymer consisting essentially of the repeat units $$-CF_2-CF_2- \quad \text{(I)}$$

and

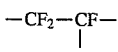

$$-CF_2-CF- \atop | \atop OCH_2CF_2(CF_2)_nQ \quad \text{(II)}$$

wherein:
Q is $-SO_3M$, $-SCl$, $-SO_2Cl$ or $-SR^1$;
n is an integer of 1 to 10;
M is hydrogen, an alkali metal cation or an ammonium ion; and
$R^1$ is an alkyl group containing 1 to 10 carbon atoms;

and provided that the molar ratio of (I):(II) is 0:100 to about 99:1.

This invention also provides a compound of the formula

$$CF_2=CFOCH_2CF_2(CF_2)_nSR^1 \quad \text{(V)}$$

wherein $R^1$ is an alkyl group containing 1 to 10 carbon atoms; and n is an integer of 1 to 10.

Also disclosed herein is a process to make a partially fluorinated polymer, comprising:

reacting tetrafluoroethylene, carbon dioxide, and an alkali metal thioalkoxide to obtain the alkali metal salt of a thio-containing partially fluorinated alkali metal carboxylate, and reacting said carboxylate with a dialkyl sulfate to obtain an ester of a thio-containing partially fluorinated carboxylic acid; or reacting tetrafluoroethylene, an alkali metal thioalkoxide and a dialkyl carbonate to obtain said ester;

reducing said ester with a suitable reducing agent to the corresponding thio-containing partially fluorinated alcohol;

reacting said alcohol with a base capable of forming an alkoxide anion from said alcohol, and tetrafluoroethylene, to form a monomer of the formula $CF_2=CFOCH_2CF_2CF_2SR^1$;

free radically polymerizing said monomer, optionally with tetrafluoroethylene comonomer, to form a thio-containing polymer;

reacting said thio-containing polymer with a sufficient amount of chlorine at a temperature of about 80° C. to about 140° C. for a period of time sufficient to form a sulfenyl chloride containing polymer; and reacting said sulfenyl chloride containing polymer with a sufficient amount of chlorine and water, at a temperature of about 80° C. to about 140° C., for a period of time sufficient to form a sulfonyl chloride containing polymer; and converting said sulfonyl chloride containing polymer to a sulfonic acid, alkali metal sulfonate, or ammonium sulfonate by reaction with water, an alkali metal base or an amine, respectively;

and wherein $R^1$ is alkyl containing 1 to 10 carbon atoms.

Described herein is a process for producing a sulfonyl chloride or sulfonic acid containing polymer, comprising, (a) contacting at 80° C. to about 140° C., a sufficient amount of chlorine with a polymer consisting essentially of the repeat units $$-CF_2-CF_2- \quad \text{(I)}$$

and

$$-CF_2-CF- \atop | \atop OCH_2CF_2(CF_2)_nSR^1 \quad \text{(III)}$$

for a period of time sufficient to produce a polymer consisting essentially of the repeat units $$-CF_2-CF_2- \quad \text{(I)}$$

and

$$-CF_2-CF- \atop | \atop OCH_2CF_2(CF_2)_nSCl \quad \text{(IV)}$$

(b) contacting at 80° C. to about 140° C., a sufficient amount of chlorine and water with a polymer consisting essentially of repeat units (I) and (IV) for a period of time sufficient to produce a polymer consisting essentially of the repeat units $$-CF_2-CF_2- \quad (I)$$

and $$\begin{array}{c} -CF_2-CF- \\ | \\ OCH_2CF_2(CF_2)_nT \end{array} \quad (VI)$$

or carrying (a) and (b) simultaneously on a polymer consisting essentially of repeat units (I) and (III) to produce a polymer consisting essentially of repeat units (I) and (VI);

wherein n is an integer of 1 to 10; $R^1$ is an alkyl group containing 1 to 10 carbon atoms; and T is $SO_2Cl$ or $SO_3H$;

and provided that the molar ratio of (I):(III) is 0:100 to about 99:1.

DETAILS OF THE INVENTION

The synthesis of the final partially fluorinated sulfonic acid (or sulfonate) containing polymers described herein can be done by a series of reactions. Some of these reactions are known. For instance the following reactions would be applicable when n is >1.

$$R^1SNa+I(CF_2)_nI \rightarrow R^1S(CF_2)_nI \quad (A)$$

$$R^1S(CF_2)_nI+H_2C=CH_2 \rightarrow R^1S(CF_2)_nCH_2CH_2I \quad (B)$$

$$R^1S(CF_2)_nCH_2CH_2I \rightarrow R^1S(CF_2)_nCH=CH_2 \quad (C)$$

$$R^1S(CF_2)_nCH=CH_2 \rightarrow R^1S(CF_2)_nCOOH \quad (D)$$

$$R^1S(CF_2)_nCOOH \rightarrow R^1S(CF_2)_nCH_2OH \quad (E)$$

Once the product of E is obtained, the synthesis can proceed similarly to that shown in (5a) and (5b), below. The following papers contain information on the above reactions:

(A) C. Wakselman, et al., in "Organofluorine Chemistry. Principles and Commercial Applications", R. E. Banks, et al., (ed.), Plenum Press, New York, 1994, p. 182.

(B) and (C) Ibid., p. 189.

(D) M. Hudlicky, "Chemistry of Organic Fluorine Compounds", Ellis Horwood, Ltd., 1976, p. 210, using potassium permanganate as the oxidant.

(E) Ibid., p. 180, using $LiAlH_4$ or $NaBH_4$ as the reducing agents.

One method to obtain the vinyl ether monomer (V) is to first prepare an alcohol of the formula $HOCH_2CF_2(CF_2)_nSR^1$ (VI), wherein n and $R^1$ are as defined above. For instance, when n is 1, (VI) can be obtained by either of the following reaction sequences:

$$R^1SNa+CF_2=CF_2+CO_2 \rightarrow R^1SCF_2CF_2CO_2Na \quad (1)$$

$$R^1SCF_2CF_2CO_2Na+(R^2O)_2SO_2 \rightarrow R^1SCF_2CF_2CO_2R^2 \quad (2)$$

or $$R^1SNa+CF_2=CF_2+(R^2O)_2C=O \rightarrow R^1SCF_2CF_2CO_2R^2 \quad (3)$$

then $$R^1SCF_2CF_2CO_2R^2+NaBH_4 \rightarrow R^1SCF_2CF_2CH_2OH \quad (4)$$

Reactions similar to (1) and (2) are described in U.S. Pat. No. 4,474,700, col. 4, line 67 to col. 5, line 3 (which is hereby included by reference), while reactions similar to (3) are described in U.S. Pat. Nos. 4,597,913 and 4,555,369 (which are hereby included by reference). While not critical, reaction (3) may be carried out at about 0° C. to about 100° C., and reaction (4) at about 0° C. to about 50° C. The same solvents for (1) and (2), as recited in U.S. Pat. No. 4,474,700 may be used for (3). For (4), it is preferred to run the reaction in water or a lower alcohol, such as ethanol, or a mixture of the two. In reaction (4) alkali metal borohydrides are suitable reducing agents, but $LiAlH_4$ or hydrogen in the presence of a suitable catalyst may also be used under conditions known to the artisan.

The alcohol formed in reaction (4) may be converted to the vinyl ether by $$R^1SCF_2CF_2CH_2OH+NaH \rightarrow R^1SCF_2CF_2CH_2O^-Na^+ \quad (5a)$$

$$R^1SCF_2CF_2CH_2O^-Na^++CF_2=CF_2 \rightarrow \\ R^1SCF_2CF_2CH_2OCF=CF_2 \quad (5b)$$

Reactions (5a) and (5b) may be carried out in sequence in a single reactor. Any suitable base that will produce the appropriate alkoxide anion in a reaction such as (5a) may be used, such as an alkali metal hydride or metal alkyl. Reaction (5a) may be carried out at a temperature of about 0° C. to about 50° C., which reaction (5 b) can be carried out at about 25° C. to about 100° C. The pressure range and solvents which are useful for (5b) include those listed in U.S. Pat. No. 4,474,700, supra. Dioxane is also a useful solvent.

Compounds of formula (V), such as the product of reaction (5b) may be homopolymerized or copolymerized with TFE, using standard free radical polymerization techniques, see for instance U.S. Pat. Nos. 4,273,728, 4,273,729 and 4,275,225, which are hereby included by reference. The polymerizations may be conducted neat, in the presence of an organic liquid (which may or may not be solvent for any of the starting materials and/or product polymer, and which preferably does not cause appreciable chain transfer), or in aqueous suspension or emulsion. For instance, a polymerization may be run in 1,1,2-trichlorotrifluoroethane using perfluoropropionyl peroxide as the free radical initiator. Polymerization temperature is chosen depending on the type of initiator and is generally in the range of 0° C. to about 150° C. Preferred temperatures are from about 25° C. to about 100° C. Polymerizations are generally run in a closed pressure vessel so as to minimize loss of volatile or gaseous monomers, in the absence of oxygen and at autogenous pressures.

The (co)polymer produced by the (co)polymerization of (V) is soluble in organic solvents, and so is useful as a chemically resistant coating or encapsulant. The coating may be made by applying the solution to the surface to be coated by brushing, spraying or rolling etc., of a solution of the polymer, and the solvent allowed to evaporate. An article may be encapsulated by dipping or otherwise completely coating the article with a polymer solution and allowing the solvent to evaporate.

The (co)polymers of (V) are also useful as intermediates for the preparation of a sulfonic acid containing (co)polymer which is useful as an ion-exchange resin or an acid catalyst. The sulfonic acid is produced by oxidation of thio group present in the (co)polymer. When this oxidation is carried out it is important that the reactions used to produce the sulfonic acid group are selective so that the —$CH_2$— group in the polymer is not oxidized or otherwise chemically changed. This is somewhat different from the analogous thio-containing perfluorinated polymers, which are overall much more resistant to such oxidations or other side reactions.

Continuing with the polymer of the product of reaction (5b), this oxidation may be accomplished by the following reactions (only the appropriate sulfur group is shown on the polymer—the remainder of the polymer is chemically unaffected)

$$—CH_2CF_2CF_2SR^1 + Cl_2 \rightarrow —CH_2CF_2CF_2SCl \quad (6a)$$

$$—CH_2CF_2CF_2SCl + Cl_2 + H_2O \rightarrow —CH_2CF_2CF_2SO_2Cl \quad (6b)$$

$$—CH_2CF_2CF_2SO_2Cl + H_2O \rightarrow —CH_2CF_2CF_2SO_3H \quad (6c)$$

The product of reaction (6c) may be converted to an alkali metal or ammonium sulfonate by reaction with an appropriate base, such as sodium hydroxide, potassium carbonate, or ammonium hydroxide.

For reaction (6a) the minimum amount of chlorine desired is the stoichiometric amount, but it is preferred if there is a 2 to 5 fold excess of chlorine present. For reaction (6b) it is desirable to have at least the stoichiometric amounts of water and chlorine present, but it is preferred if the water is present in 2 to 20 fold excess, and the chlorine is present in 2 to 5 fold excess. Reaction (6b) may also be conducted in the presence of an organic acid, such as acetic acid or trifluoroacetic acid, or in an inert organic solvent such as 1,1,2-trichloro-1,2,2-trifluoroethane. Reaction (6a) and (6b) are preferably done is a closed pressure vessel so as to minimize the loss of volatile reagents, and under autogenous pressure. Reaction (6b) is preferably done is a vessel constructed of glass or an inert polymeric material such as polytetrafluoroethylene, to minimize formation of corrosion products which may be foraged in metal reactors. In both reactions, having at least a stoichiometric amount of each reagent present ensures at least the possibility that all of the thio groups will be converted to sulfonyl chloride groups.

For reaction (6c), typical hydrolysis conditions for sulfonyl chlorides are used, which involves contact of the sulfonyl chloride with water and a base such as sodium, potassium or ammonium hydroxide. Ambient temperatures are convenient, although temperatures up to 75° C. may be used to accelerate the hydrolysis reaction. If sufficient base is used to form the sulfonate salt, the sulfonic acid may be may be made by addition of a strong acid.

The resulting sulfonyl chloride containing polymer consists essentially of repeat unit repeat unit (IV), and optionally repeat unit (I). The polymer wherein corresponding unit is a sulfonic acid or sulfonate group consists essentially of the repeat unit (II), and optionally repeat unit (I). In both instances "consisting essentially of" includes polymers with small amounts of residual (unconverted) thio, sulfenyl chloride, and/or sulfonyl chloride groups.

In some preferred polymers containing repeat unit (II), repeat unit (I) is also present. In these polymers it is preferred that the molar ratio of (I):(II) in the polymer is about 1:99 to about 99:1, more preferably about 1:10 to about 10:1. In another preferred polymer, the ration of (I):(II) is 0:100.

In all of the compounds and polymers herein, as applicable: it is preferred that all alkyl or substituted alkyl groups contain 1 to 10 carbon atoms, and more preferred if such alkyl groups are methyl groups; it is also preferred if $R^1$ is alkyl, especially methyl; and it is preferred if n is 1.

EXAMPLE 1

Synthesis of $CH_3SCF_2CF_2CO_2CH_3$

A 400 mL pressure vessel was charged with 34.1 g (0.49 mol) of sodium thiomethoxide and 150 mL of anhydrous dimethylsulfoxide (DMSO). The vessel was closed, cooled in dry ice, evacuated and charged with 32 g (0.73 mol) of carbon dioxide and 50 g (0.5 mol) of tetrafluoroethylene. The vessel contents were heated with agitation to 50° C. for 1 hr and 100° C. for 5 hr. After cooling to room temperature, the vessel contents were transferred to a 500 mL round bottom flask using an additional 30 mL of DMSO to rinse. Dimethylsulfate (65 g, 0.52 mol) was added and the mixture was stirred for 3 hr at 30°–50° C. Volatiles were removed by distillation at 1 mm into a dry ice cooled receiver with a maximum pot temperature of 65 ° C.

The volatiles collected from eight reactions were combined, washed with water and dried over anhydrous magnesium sulfate. Distillation through an 18 inch Vigreaux column gave 547 g (80% ) of colorless liquid, bp 88° C. at 60 mm. $^1$H NMR ($\delta$, $CDCl_3$) 2.38 (s, 3H), 3.96 (s, 3H); $^{19}$F NMR ($\delta$, $CDCl_3$) –92.5 (t, 2F), –117.0 (t, 2F).

EXAMPLE 2

Synthesis of $CH_3SCF_2CF_2CH_2OH$

The ester $CH_3SCF_2CF_2CO_2CH_3$ (546 g, 2.65 mol) was added dropwise over 3 hr to a solution of 100.2 g (2.65 mol) of sodium borohydride in 920 mL of ethanol which was cooled in an ice water bath. After the addition was complete the mixture was allowed to warm to room temperature over 1 hr. The mixture was cooled in ice water and cautiously hydrolyzed by addition of 1.4 L of 6N hydrochloric acid. The mixture was diluted to 5-L with water and a lower layer was collected. The aqueous solution was extracted with 500 mL of methylene chloride. The organic layers were washed with 1-L of water and dried over anhydrous magnesium sulfate. The methylene chloride was removed by distillation at atmospheric pressure through an 18 inch Vigreaux column. Distillation of the residue through the same column gave 372.5 g (79 %) of colorless liquid, bp 35°–38° C. at 0.15 mm. $^1$H NMR ($\delta$, $CDCl_3$) 2.58 (s, 3H), 2.88 (t, 1H), 4.05 (m, 2H); $^{19}$F NMR ($\delta$, $CDCl_3$) –92.7 (t, 2F), –121.7 (m 2F).

EXAMPLE 3

Synthesis of $CH_3SCF_2CF_2CH_2OCF=CF_2$

The alcohol $CH_3SCF_2CF_2CH_2OH$ (53.4 g, 0.3 mol) was added dropwise to a suspension of 8.75 g of 95% sodium hydride in 100 mL of anhydrous dioxane which was cooled in an ice water bath. This mixture was stirred overnight at room temperature and transferred to a 400 mL stainless steel pressure vessel using an additional 40 mL of dioxane to rinse. The vessel was closed, cooled in dry ice, evacuated, charged with 50 g of tetrafluoroethylene, warmed to 50° C. and agitated for 18 hr. The vessel was vented to atmospheric pressure at room temperature and its contents were poured into 1 L of ice water containing 25 mL of concentrated hydrochloric acid. The lower layer was separated and washed with 500 mL of ice water.

The combined product from seven runs was washed again with 2×500 mL of ice water and distilled through a 16 inch Vigreaux column. A liquid weighing 371 g was collected with a boiling point of 50°–52° C. at 20–25 mm. This product in two portions was chromatographed through columns of 1 Kg silica gel, packed in pentane. The columns were eluted with pentane. Early fractions which contained only the desired product by glpc analysis were combined and distilled through the Vigreaux column at atmospheric pressure to remove the solvent and then at reduced pressure to give 291.8 g of product, bp 54°–55° C. at 26 mm which was a minimum of 99.5% pure by glpc analysis. An additional 51 g of product which was 95% pure by glpc analysis was obtained from latter chromatography cuts. $^1$H NMR ($\delta$, CDCl$_3$) 2.39 (s, 3H), 4.38 (t, 2H); $^{19}$F NMR ($\delta$, CDCl$_3$) −92.6 (s, 2F), −120.1 (m 2F), −121.8 (dd, 1F), −127.5 (dd, 1F), −137.0 (dd, 1F). Another sample prepared in the same fashion was submitted for elemental analysis.

Anal. Calcd. for C$_6$H$_5$F$_7$OS: C, 27.91; H, 1.95; F, 51.52; S, 12.43. Found: C, 27.89; H, 2.04; F, 52.32; S, 12.34.

EXAMPLE 4

Polymerization of CH$_3$SCF$_2$CF$_2$CH$_2$OCF=CF$_2$

A 50 mL round bottom flask was charged with 5.8 g of CH$_3$SCF$_2$CF$_2$CH$_2$OCF=CF$_2$ and 10 g of 1,1,2-trichlorotrifluoroethane. This solution was frozen, and the reactor vessel was evacuated and filled with argon several times. A solution (1.0 mL) of about 0.025M (CF$_3$CF$_2$CF$_2$OCF(CF$_3$)CO$_2$)$_2$ in CF$_3$CF$_2$CF$_2$OCFHCF$_3$ was added at −30° C. The solution was allowed to slowly warm to room temperature and stirred for 72 hr. It was poured into 300 mL of hexane which was cooled in dry ice. The hexane was decanted from the solid polymer which was dried in a vacuum oven at 125° C. to give 4.3 g of clear glass. DSC analysis showed a Tg at about 14° C. on the second heat and no melting peak.

EXAMPLE 5

Copolymerization of CH$_3$SCF$_2$CF$_2$CH$_2$OCF=CF$_2$ and Tetrafluoroethylene in a 1:2 Molar Ratio An 80 mL pressure vessel was cooled in dry ice and charged with 19 g of CH$_3$SCF$_2$CF$_2$CH$_2$OCF=CF$_2$, 44 g of 1,1,2-trichlorotrifluoroethane and 10 mL of a solution of about 0.025M (CF$_3$CF$_2$CF$_2$OCF(CF$_3$)CO$_2$)$_2$ in CF$_3$CF$_2$CF$_2$OCFHCF$_3$. The tube was closed, evacuated and charged with 15 g of tetrafluoroethylene. The tube was allowed to warm without external heating. Internal pressure reached a maximum of about 1 MPa at 19° C. and fell over the course of several hours to 0.2 MPa at 26° C. The reactor was vented to atmospheric pressure and a thick clear gel in the reactor was dissolved in about 800 mL of 1,1,2-trichlorotrifluoroethane. This solution was filtered, concentrated to about 500 mL and added slowly to 800 mL of hexane which was cooled in dry ice. The solid precipitate was collected, dried under a heat lamp and then in a vacuum oven at 125° C. to give 27.3 g of white polymer which could be pressed at 80° C. to a clear tough film. Inherent viscosity in 1,1,2-trichlorotrifluoroethane was 0.24 dl/g. $^1$H NMR ($\delta$, CCl$_2$FCClF$_2$) 2.35 (s, 3H), 4.42 (t, 2H); $^{19}$F NMR ($\delta$, CDCl$_3$) −92.9 (s, CF$_2$S), −135 to −137.5 (tertiary F), −117 to −122.5 (CF$_2$ groups). By integration of absorptions at −92.9 and −135 to −137.5 versus the other absorptions, the ratio of CH$_3$SCF$_2$CF$_2$CH$_2$OCF=CF$_2$ to tetrafluoroethylene in the polymer was 1 to 1.82. DSC analysis showed a T$_g$ at 5.4° C. on the second heat and no melting peak. Another polymer sample prepared in similar fashion using perfluoropropionyl peroxide as initiator had an inherent viscosity of 0.197 and about a 1:2 ratio of monomers as calculated from its $^{19}$F NMR spectrum.

Anal. Calc. for 1:2 copolymer: C, 26.21; H, 1.10; F, 62.20; S, 6.99. Found: C, 25.67; H, 1.15; F, 61.91; S, 6.94.

A third sample of this copolymer was prepared using 29 g of 1,1,2-trichlorotrifluoroethane and 5 mL of the 0.025M (CF$_3$CF$_2$CF$_2$OCF(CF$_3$)CO$_2$)$_2$ in CF$_3$CF$_2$CF$_2$OCFHCF$_3$ initiator solution. This material had an inherent viscosity of 0.30 dL/g.

EXAMPLE 6

Copolymerization of CH$_3$SCF$_2$CF$_2$CH$_2$OCF=CF$_2$ and Tetrafluoroethylene in a 1:4 Molar Ratio Following the procedure of Example 5, a mixture of 14.5 g CH$_3$SCF$_2$CF$_2$CH$_2$OCF=CF$_2$, 5 mL of a solution of about 0.025M (CF$_3$CF$_2$CF$_2$OCF(CF$_3$)CO$_2$)$_2$ in CF$_3$CF$_2$CF$_2$OCFHCF$_3$ and 23 g of tetrafluoroethylene was allowed to react for about 13 hr at a maximum temperature of 28° C. The resulting gel was washed several times with 1,1,2-trichlorotrifluoroethane and dried at 120° C. in a vacuum oven to give 26.5 g of a colorless solid polymer which could be pressed to a clear film at 225° C. DSC analysis showed no thermal events from 0° to 350° C. on the second heating. The polymer was determined to contain 82.3 mole % of tetrafluoroethylene and 17.7 mole % of the sulfur containing comonomer by integration of appropriate resonances in its fluorine NMR spectrum, measured in hexafluorobenzene solution at 80° C.

EXAMPLE 7

Conversion of the —CF$_2$SCH$_3$ Side Chain to —CF$_2$SCl

A 2.9 g sample of polymer from Example 5 was dissolved in 50 mL of 1,1,2-trichlorotrifluoroethane in a heavy walled glass tube. The tube contents were frozen and the tube was evacuated, charged with 3.5 mL of liquid chlorine and sealed. The tube was heated in an oven at 120° C. for 14 hr. It was cooled in dry ice and acetone, opened and the clear solution was concentrated under vacuum at 40° C. to a white opaque solid. A proton NMR spectrum of the solid in 1,1,2-trichlorotrifluoroethane showed the presence of a triplet at 4.46 ppm for the pendant OCH$_2$ group and the nearly complete absence of the SCH$_3$ signal at 2.35 ppm.

EXAMPLE 8

Conversion of the —CF$_2$SCl Side Chain to —CF$_2$SO$_2$Cl

The product from Example 7 in 50 mL of 1,1,2-trichlorotrifluoroethane was sealed into a heavy-walled glass tube with 20 mL of water and 4 mL of liquid chlorine. The tube was heated in an oven at 100° C. for 16 hr and at 120° C. for 16 hr. The organic layer was isolated and concentrated under vacuum to 2.87 g of light yellow solid. An infrared spectrum of the solid showed a band at 1421 cm$^{-1}$ suggesting the presence of the CF$_2$SO$_2$Cl group.

EXAMPLE 9

Copolymerization of CH$_3$SCF$_2$CF$_2$CH$_2$OCF=CF$_2$ and Tetrafluoroethylene

An 80-mL Hastelloy® pressure vessel was cooled in dry ice, flushed with argon and charged with 19.3 g of CH$_3$SCF$_2$CF$_2$CH$_2$OCF=CF$_2$, 29 g of 1,1,2-trichlorotrifluoroethane and 1-ml of and approximately 0.025M solution of (CF$_3$CF$_2$CF$_2$OCF(CF$_3$)CO$_2$)$_2$ in CF$_3$CF$_2$CF$_2$OCHFCF$_3$. The vessel was closed, evacuated and charged with 15 g of tetrafluoroethylene. The vessel was agitated while being allowed to warm to room temperature overnight. The vessel was vented, the contents were diluted with additional 1,1, 2-trichlorotrifluoroethane, filtered and concentrated in vacuum to 8.03 g of solid polymer. The polymer was dissolved in 1,1,2-trichlorotrifluoroethane and poured slowly into pentane which was chilled to −40° C. The solid polymer was isolated and dried under vacuum affording 7.36 g of polymer with an inherent viscosity (1,1,2-trichlorotrifluoroethane) of 0.48 dL/g. Its proton and fluorine NMR spectra were as described in Example 5 and the molar ratio of $CH_3SCF_2CF_2CH_2OCF=CF_2$ to tetrafluoroethylene units in the polymer was calculated as 2:3.

EXAMPLE 10

Polymerization of $CH_3SCF_2CF_2CH_2OCF=CF_2$

A 50-mL round bottom flask was charged with 10.3 g of the title monomer and evacuated and filled with argon four times. The flask was cooled in a dry ice bath and 1 mL of a solution of about 0.035M $(CF_3CF_2CF_2OCF(CF_3)CO_2)_2$ in $CF_3CF_2CF_2OCHFCF_3$ was added. This solution was allowed to stir for 48 hr at 0° C., warmed over one day to room temperature, stirred for one day at room temperature and warmed to 50° C. for 3 hr. It was cooled to −5° C. and a second 1-mL portion of the peroxide initiator solution was added. This mixture was allowed to warm to room temperature over 1 day and heated to 50° C. for 3 hr. The product was dissolved in tetrahydrofuran (THF) and precipitated by adding to 500 mL of pentane which had been cooled to −40° C. The freely divided solid was collected, dissolved in THF and evaporated under vacuum giving 6.23 g of polymer. Inherent viscosity in THF was 0.19 dl/g. Analysis by gel permeation chromatography in THF showed $M_n$=34300 and $M_w$= 94300 versus poly(methyl methacrylate) standards. An $M_w$ of 94300 g/mol was measured by laser light scattering in toluene solution. $^1H$ NMR ($\delta$, THF-$D_8$) 2.4 (3H), 4.5 (2H). $^{19}F$ NMR ($\delta$, THF-$D_8$) −92.1 (2F, $CF_2S$), −109 to −119 (2F, backbone $CF_2$), −119.1 (2F, $CH_2CF_2$), −130 to −133.5 (1F).

EXAMPLE 11

Emulsion Homopolymerization of $CH_3SCF_2CF_2CH_2OCF=CF_2$

A 1-L round bottom flask was swept with argon and charged with 200 mL of deoxygenated water, 1.9 g of ammonium perfluorononanoate, 12.9 g of the title monomer and 2 g of $Na_2HPO_4 \cdot 7H_2O$. This mixture was stirred vigorously at room temperature and 0.052 g of sodium bisulfite and 0.057 g of ammonium persulfate were added. This mixture was stirred for 24 hr at room temperature. An additional 0.052 g of sodium bisulfite and 0.057 g of ammonium persulfate were added and this mixture was stirred for 24 hr at room temperature. The emulsion was diluted with 200 mL of distilled water and frozen in dry ice. After thawing, the mixture was filtered and the solid was washed with 2×500 mL of water and dried under vacuum giving 11.8 g of white solid polymer. Inherent viscosity in THF was 0.069 dL/g and the proton and fluorine NMR spectra were as described in Example 10.

EXAMPLE 12

Conversion of the —$SCH_3$ Group to —SCl in the $CH_3SCF_2CF_2CH_2OCF=CF_2$ Homopolymer A 400 mL Hastelloy pressure vessel was charged with 2.0 g of a homopolymer of $CH_3SCF_2CF_2CH_2OCF=CF_2$ (prepared as described in Example 10 with an inherent viscosity of 0.12) and 150 mL of 1,1,2-trichlorotrifluoroethane. The vessel was closed, cooled with dry ice and charged with 12 g of chlorine. The vessel contents were heated to 90° C. for 2 hr and 125° C. for 18 hr. The vessel was cooled and vented to atmospheric pressure. The light yellow solution was concentrated under vacuum to 1.81 g of solid. Its proton NMR spectrum in 1,1,2-trichlorotrifluoroethane showed absorption at 4.5 ppm for the —$OCH_2$— group and a small peak at 4.85 ppm assigned to an —$SCH_2Cl$ impurity. There was no absorption detected for the $SCH_3$ group which is present in the starting polymer.

EXAMPLE 13

Conversion of the —$SCH_3$ Group to —$SO_2Cl$ in the $CH_3SCF_2CF_2CH_2OCF=CF_2$ Homopolymer A 210 mL Hastelloy® pressure vessel was charged with 5.0 g of the homopolymer of $CH_3SCF_2CF_2CH_2OCF=CF_2$ (prepared as described in Example 10 with an inherent viscosity of 0.15) and 100 mL of carbon tetrachloride. The vessel was closed, cooled with dry ice and charged with 15 g of chlorine. The vessel contents were heated to 125° C. for 18 hr. The vessel was cooled and vented to atmospheric pressure. The clear light yellow solution from the pressure vessel was bubbled with nitrogen for a few minutes to remove excess chlorine. A proton NMR spectrum of the solution showed a peak at 4.42 ppm (—$OCH_2$—) and the complete absence of the $CH_3$ resonance of the starting polymer. $^{19}F$ NMR ($\delta$, $CCl_4$) −93.7 (2F, $CF_2S$), −113.0 (2F, backbone $CF_2$), −118.0 (2F, $CH_2CF_2$), −130 to −133.5 (1F).

About one-half of the above carbon tetrachloride solution was diluted to 100 mL with carbon tetrachloride and transferred to a 500 mL creased flask. Aliquat® 336 surfactant (0.1 g) (Janssen Chimica) was added, followed by 100 mL of an aqueous sodium hypochlorite solution. This mixture was stirred vigorously for 1 hour at room temperature and for 3 hours at 40° C. After standing overnight, the mixture was filtered and the solid polymer was dried at 100° C. and 0.05 mm giving 2.61 g of white solid which was insoluble in carbon tetrachloride and 1,1,2-trichlorotrifluoroethane. An infrared spectrum of the solid showed a strong band at 1415 $cm^{-1}$ confirming presence of the $SO_2Cl$ group.

What is claimed is:

1. A polymer consisting essentially of the repeat units

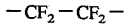
 (I)

and

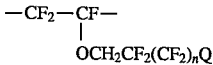
 (II)

wherein:

Q is —$SO_3M$, —SCl, —$SO_2Cl$ or —$SR^1$;

n is an integer of 1 to 10;

M is hydrogen, an alkali metal cation or an ammonium ion; and $R^1$ is an alkyl group containing 1 to 10 carbon atoms;

and provided that the molar ratio of (I):(II) is 0:100 to about 99:1.

2. The polymer as recited in claim 1 wherein n is 1.

3. The polymer as recited in claim 1 wherein Q is $SO_3M$.

4. The polymer as recited in claim 2 wherein Q is $SO_3M$.

5. The polymer as recited in claim 3 wherein M is hydrogen.

6. The polymer as recited in claim 1 wherein the molar ratio of (I):(II) is 10:1 to about 1:10.

7. The process of using the polymer as recited in claim 3 as an ion exchange resin.

8. The polymer as recited in claim 3 wherein M is hydrogen.

9. The process of using the polymer as recited in claim 8 as an acid catalyst.

10. The polymer as recited in claim 1 wherein the ratio of (I):(II) is 0:100.

11. An ion exchange resin comprising the polymer recited in claim 3.

12. An acid catalyst comprising the polymer recited in claim 8.

* * * * *